(12) United States Patent
Vigevani et al.

(10) Patent No.: US 11,173,258 B2
(45) Date of Patent: Nov. 16, 2021

(54) USING PIEZOELECTRIC ELECTRODES AS ACTIVE SURFACES FOR ELECTROPLATING PROCESS

(71) Applicant: Analog Devices, Inc., Norwood, MA (US)

(72) Inventors: Gabriele Vigevani, Brookline, MA (US); Xin Zhang, Acton, MA (US)

(73) Assignee: Analog Devices, Inc., Wilmington, MA (US)

( * ) Notice: Subject to any disclaimer, the term of this patent is extended or adjusted under 35 U.S.C. 154(b) by 111 days.

(21) Appl. No.: 16/270,481

(22) Filed: Feb. 7, 2019

(65) Prior Publication Data

US 2020/0069890 A1 Mar. 5, 2020

Related U.S. Application Data

(60) Provisional application No. 62/725,221, filed on Aug. 30, 2018.

(51) Int. Cl.
*A61M 11/00* (2006.01)
*H01L 41/047* (2006.01)
(Continued)

(52) U.S. Cl.
CPC ......... *A61M 11/005* (2013.01); *A61M 11/003* (2014.02); *A61M 15/0021* (2014.02);
(Continued)

(58) Field of Classification Search
CPC . B05B 17/06; B05B 17/0607; B05B 17/0638; A61M 11/005; A61M 11/003;
(Continued)

(56) References Cited

U.S. PATENT DOCUMENTS 7,178,906 B2 2/2007 Drury et al.
7,545,246 B2 6/2009 Kim et al.
(Continued)

FOREIGN PATENT DOCUMENTS

CN 1408551 A 4/2003
WO WO 2013/155513 A1 10/2013
(Continued)

OTHER PUBLICATIONS

[No Author Listed], Nebulizer Plates. Veco Precision Metal Website. Retrieved from the internet: https://www.vecoprecision.com/precision-products/nebulizer-plates. (Last accessed Mar. 21, 2019). 4 pages.
(Continued)

*Primary Examiner* — Steven J Ganey
(74) *Attorney, Agent, or Firm* — Wolf, Greenfield & Sacks, P.C.

(57) ABSTRACT

Microelectromechanical systems (MEMS) mesh-membrane nebulizers are described. The MEMS mesh-membrane nebulizers may include a piezoelectric MEMS mesh membrane. The piezoelectric MEMS mesh membrane may include a piezoelectric active layer patterned with openings for making droplets. One electrode of the piezoelectric MEMS mesh membrane may serve as an electrode for electroplating. Activation of the piezoelectric MEMS mesh membrane may generate droplets suitable for delivery of medicines or other uses.

19 Claims, 8 Drawing Sheets

(51) Int. Cl.
| | |
|---|---|
| *H01L 41/053* | (2006.01) |
| *H01L 41/09* | (2006.01) |
| *H01L 41/187* | (2006.01) |
| *H01L 41/23* | (2013.01) |
| *C25D 5/54* | (2006.01) |
| *H01L 41/316* | (2013.01) |
| *H01L 41/332* | (2013.01) |
| *A61M 15/00* | (2006.01) |
| *C25D 7/12* | (2006.01) |
| *H01L 41/29* | (2013.01) |
| *B05B 17/06* | (2006.01) |
| *B05B 17/00* | (2006.01) |

(52) U.S. Cl.
CPC ......... *A61M 15/0085* (2013.01); *B05B 17/06* (2013.01); *B05B 17/0607* (2013.01); *B05B 17/0638* (2013.01); *C25D 5/54* (2013.01); *C25D 7/12* (2013.01); *H01L 41/0477* (2013.01); *H01L 41/0533* (2013.01); *H01L 41/0973* (2013.01); *H01L 41/187* (2013.01); *H01L 41/23* (2013.01); *H01L 41/29* (2013.01); *H01L 41/316* (2013.01); *H01L 41/332* (2013.01)

(58) Field of Classification Search
CPC . A61M 15/0021; A61M 15/0085; C25D 5/54; C25D 7/12; H01L 41/0477; H01L 41/0533; H01L 41/0973; H01L 41/187; H01L 41/23; H01L 41/29; H01L 41/316; H01L 41/332
USPC .............. 239/4, 102.1, 102.2, 552, 596, 601
See application file for complete search history.

(56) References Cited

U.S. PATENT DOCUMENTS

| | | | |
|---|---|---|---|
| 8,684,980 | B2 | 4/2014 | Hunter et al. |
| 9,814,098 | B2 | 11/2017 | Gruenbacher et al. |
| 2004/0050947 | A1 | 3/2004 | Power et al. |
| 2009/0244203 | A1 | 10/2009 | Mita |
| 2010/0079523 | A1 | 4/2010 | Bibl et al. |
| 2015/0075521 | A1 | 3/2015 | Lee et al. |
| 2015/0079670 | A1 | 3/2015 | Domansky et al. |
| 2016/0058960 | A1 | 3/2016 | Papania et al. |
| 2017/0368828 | A1* | 12/2017 | Naganuma ............. B41J 2/1643 |
| 2017/0373242 | A1 | 12/2017 | Yamada et al. |
| 2018/0086077 | A1 | 3/2018 | Yokoyama et al. |
| 2020/0220520 | A1* | 7/2020 | Stokes ................... H03H 9/173 |

FOREIGN PATENT DOCUMENTS

| | | |
|---|---|---|
| WO | WO 2013/186031 A2 | 12/2013 |
| WO | WO 2017/149165 A1 | 9/2017 |

OTHER PUBLICATIONS

Choi et al., Fabrication and Characterization of Medical Mesh-Nebulizer for Aerosol drug Delivery. Applied Sciences. 2018; 8(4):604. 12 pages.

Tadigadapa, Piezoelectric Microelectromechanical Systems—Challenges and Opportunities. Procedia Engineering. 2010; 5:468-471.

Wang, Investigation for Improvement and Application of MEMS-Based Micro-Electro-Discharge Machining ($M^3$EDM). Thesis Submitted in Partial Fulfillment of the Requirements for the Degree of Master of Applied Science. The University of British Columbia, Jan. 2011. 84 pages.

* cited by examiner

USING PIEZOELECTRIC ELECTRODES AS ACTIVE SURFACES FOR ELECTROPLATING PROCESS

RELATED APPLICATIONS

This application claims the benefit under 35 U.S.C. § 119(e) of U.S. Provisional Application Ser. No. 62/725,221, filed Aug. 30, 2018, and entitled "USING PIEZOELECTRIC ELECTRODES AS ACTIVE SURFACES FOR ELECTROPLATING PROCESS," which is hereby incorporated herein by reference in its entirety.

FIELD OF THE DISCLOSURE

The present application relates to microelectromechanical systems (MEMS) devices.

BACKGROUND

Nebulizers for healthcare applications are devices that convert liquid drugs into medical aerosol. The aerosol is inhaled into the lungs and directly absorbed into the blood stream. The control of droplet size is a crucial parameter in delivering the drug to the lungs.

Some nebulizers are fabricated by manual assembly of a number of discrete components, including a mesh membrane, a holder, and a lead zirconate titanate (PZT) ring. The mesh membrane and the PZT ring are attached or mechanically coupled to the holder. Actuation of the PZT ring in a radial direction causes the holder to oscillate radially, which in turn causes the mesh membrane to vibrate. Vibration of the mesh membrane leads to generation of aerosol from a liquid drug placed below the holder.

BRIEF SUMMARY

MEMS-based mesh membrane devices are described. In some embodiments, a nebulizer may include a piezoelectric MEMS device having a piezoelectric layer and an electrode serving as a foundation for electroplating. A metal layer deposited on the electrode can facilitate out-of-plane motion (in an up-down direction) of the piezoelectric layer and pump liquid droplets at a desired pump volume.

In certain embodiments, a MEMS mesh membrane nebulizer is provided that comprises a thin film piezoelectric active layer comprising a plurality of openings, first and second electrodes on opposite sides of the thin film piezoelectric active layer, and a metal layer on the second electrode having a thickness greater than the second electrode.

In certain embodiments, a MEMS nebulizer device is provided that comprises a piezoelectric layer comprising a plurality of openings, a first electrode on the piezoelectric layer, and a metal layer on the first electrode.

In certain embodiments, a method of fabricating a MEMS mesh membrane is provided that comprises forming a plurality of openings in a thin film piezoelectric active layer and an electrode on the thin film piezoelectric active layer, and electroplating a metal on the electrode.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present application provide a microelectromechanical systems (MEMS) mesh membrane nebulizer. The MEMS mesh membrane nebulizer includes a thin film piezoelectric layer and an electrode coupled to the thin film piezoelectric layer and serving as a foundation for electroplating. A plurality of openings are formed in the piezoelectric layer and the electrode to create the mesh structure. A metal layer is deposited on the electrode using electrodeposition. The electroplated metal layer can facilitate actuation of the piezoelectric layer in an out-of-plane mode for dispensing liquid droplets from a sample liquid source in close proximity to the mesh membrane.

According to an aspect of the present application, microfabrication techniques are used to manufacture a MEMS mesh membrane nebulizer. The microfabrication techniques may include thin film processing, for example of a thin film piezoelectric layer, and electrodeposition. Piezoelectric materials can be used as actuators or sensing elements in MEMS devices. In both cases an active piezoelectric material may be sandwiched between a top metal electrode and a bottom metal electrode. According to some aspects, one of the two electrodes can also be used as an active or base layer for electroplating an additional metal. With this technique, aspects of the present disclosure combine the piezoelectric actuation with the unique shapes that can be achieved with electrodeposition. Use of such techniques provides for creation of small, integrated MEMS mesh membrane nebulizers.

Various embodiments described herein offer a simple way to combine advantages of piezoelectric thin film materials with electroplating technology to build nebulizer membranes.

Figure 1A:
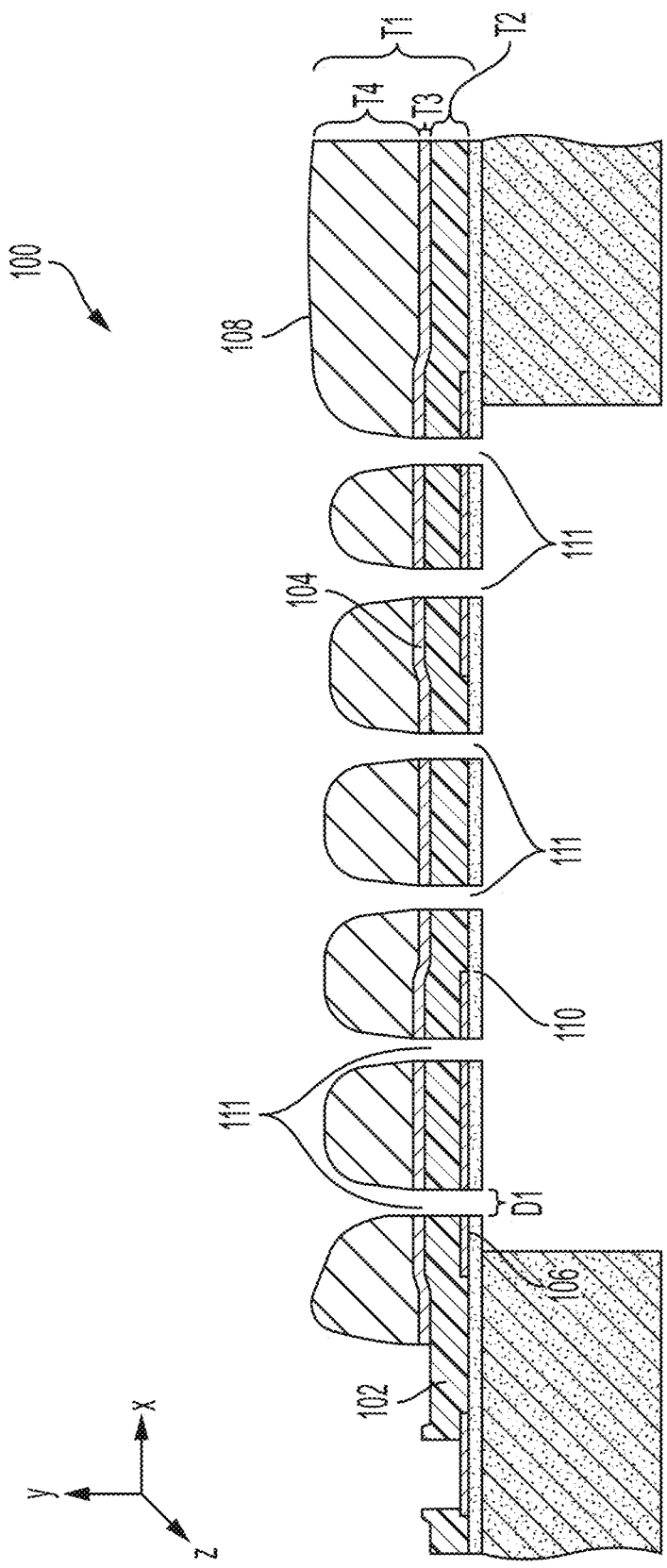
FIG. 1A illustrates a cross-section of an example MEMS mesh membrane device according to a non-limiting embodiment.

As described previously, aspects of the present application provide a MEMS mesh membrane device. FIG. 1A illustrates a cross-section of an example MEMS mesh membrane device 100 that can be used in nebulizers, according to an aspect of the disclosure. The MEMS mesh membrane device 100 includes at least a piezoelectric active layer 102, a top electrode 104, a bottom electrode 106, an electrodeposited metal layer 108, and a thermal oxide layer 110.

In a non-limiting embodiment, the piezoelectric active layer 102 may include Aluminum Nitride (AlN). In a non-limiting embodiment, thin film sputtered Aluminum Nitride may be used as the piezoelectric active layer 102. In a non-limiting embodiment, doped Aluminum Scandium Nitride (AlScN) may be used as the piezoelectric active layer 102. The piezoelectric active layer 102 may be sandwiched between the top electrode 104 and the bottom electrode 106. The electrodes may be formed from a suitable conductive material. For example, according to a non-limiting embodiment the electrodes may be formed of Molybdenum. However, other suitable conductive materials, including other metals (e.g., Aluminum, Platinum, Titanium-Tungstun (TiW)) may be used. The materials of the MEMS mesh membrane device 100 may be biocompatible in at least some embodiments. For example, the materials may lack lead, or other materials harmful to humans.

The stack of piezoelectric active layer 102, top electrode 104, and bottom electrode 106 may be small due to the microfabrication techniques used to form them. For example, the stack may have a combined thickness T1 between 1 and 10 microns, such as 2.4 microns. However, any value within that range, or any other suitable value may be used. The piezoelectric active layer 102 may have a thickness T2 of between 1 and 5 microns, such as 2 microns or any other suitable value. Each of the top electrode 104 and bottom electrode 106 may have a thickness T3 of between 0.1 and 1 microns, such as 0.2 microns. However, other thicknesses may be used for any of those components or the combined stack.

According to some aspects, the piezoelectric active layer 102 and the electrodes 104, 106 may be patterned to form a plurality of openings 111 to create the mesh structure. The openings may have any suitable size for creating liquid droplets of a desired size, as described further below with respect to the operation of the device. For example, in a non-limiting embodiment, each opening may have a diameter D1 in the range of 1-6 μm, that enable aerosol droplets of optimal size to be dispensed. In some embodiments, a plurality of the openings have a diameter D1 in the range of 1-6 μm, but not necessarily each opening may be of that size. The droplet size of 1 μm to 6 μm in some embodiments ensures an efficient and high absorption of the drug into the blood stream. While larger particles are trapped in the throat or in the delivery apparatus, smaller particles are normally exhaled and can't be absorbed in the lungs.

The piezoelectric stack (including the piezoelectric active layer 102 and the two electrodes 104, 106) serves as a substrate for electroplating. After formation of the piezoelectric stack, the top electrode 104 may be used as an active layer to enable the electroplating deposition of the metal layer 108. Electrodeposition allows for the metal layer 108 to be in direct contact with the top electrode 104. Nickel-Palladium alloys or any other metals (e.g., Chromium, Aluminum) or alloys suitable for nebulizers (e.g., being biocompatible) may be used as the metal layer 108.

According to some aspects, the thick metal layer 108 deposited on the top electrode 104 can facilitate out-of-plane motion (in the up-down direction) of the piezoelectric active layer 102 and pump liquid droplets at a desired pump volume (e.g., 130 kHz). The thick metal layer 108 not only allows for the desired pump volume to the attained (which may not be possible with only the piezoelectric stack), but also protects the piezoelectric stack from corrosion that can be caused by certain liquid drugs.

According to some embodiments, the metal layer 108 may have a thickness T4 greater than thickness T3 of the top electrode 104. The thickness T4 of the metal layer may be in a range of 40 μm-100 μm. According to a non-limiting embodiment, the thickness T4 of the metal layer 108 may be about 200 times the thickness T3 of the top electrode 104 (i.e., thickness ratio 200:1). Other suitable thickness ratios may be used. According to one aspect, the thickness T4 of the metal layer 108 may be greater than thickness T2 of the piezoelectric active layer 102. According to one aspect, the thickness T4 of the metal layer 108 may be greater than a combined thickness of the piezoelectric active layer 102 and the top electrode 104. According to one aspect, the thickness T4 of the metal layer 108 may be greater than a thickness of the piezoelectric stack.

In a non-limiting embodiment, the MEMS mesh membrane device 100 may have a diameter (or in-plane long dimension) of several mm. For example, the diameter may be between 3-4 mm, or less than 9 mm. During operation, the liquid sample 112 (shown in FIG. 1B) contacts one of the surfaces of the MEMS mesh membrane device 100 (e.g., the metal layer 108). The mesh membrane device 100 is excited to exhibit out-of-plane vibration in the y direction. Out-of-plane vibration of the piezoelectric stack builds up pressure pushing the liquid through the openings 111 and ejecting aerosol droplets 114 (e.g., in a −y direction) on the other side of the mesh membrane device.

Figure 2A:
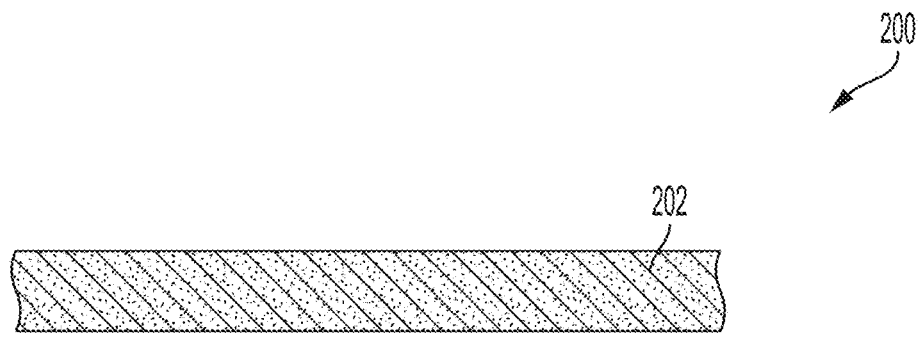
FIGS. 2A-2J illustrate a fabrication process for fabricating the MEMS mesh membrane device of FIG. 1A according to a non-limiting embodiment.
Figure 2B:
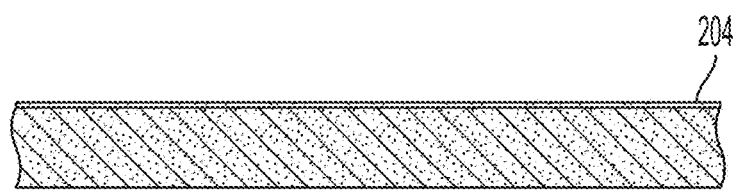

FIGS. 2A-2J illustrate a fabrication process 200 for fabricating the MEMS mesh membrane device 100 according to a non-limiting embodiment. The fabrication process 200 may begin by growing a thermal oxide layer 204 on a substrate 202 shown in FIG. 2A. The substrate 202 may be a silicon substrate. In a non-limiting embodiment, the substrate 202 may have a thickness of several microns to hundreds of microns. In some embodiments the substrate may be a wafer, and may have any suitable diameter, such as being an 8 inch wafer. In FIG. 2B, the thermal oxide layer 204 may be grown on the substrate 202. In a non-limiting embodiment, the thermal oxide layer may have a thickness of approximately 0.2 μm, although other thicknesses are possible.

Figure 2C:
Figure 2D:

As shown in FIGS. 2C and 2D, the bottom electrode 106 may be formed by depositing a suitable conductive material layer and then patterning the conductive material layer. For example, in FIG. 2C, a first conductive material layer 206 may be deposited on the thermal oxide layer 204. According to a non-limiting embodiment, the first conductive material layer 206 may be formed of Molybdenum. However, other suitable conductive materials, including other metals (e.g., Aluminum, Platinum, Titanium-Tungstun (TiW)) may be used. In a non-limiting embodiment, the first conductive material layer 206 may have a thickness of approximately 0.2 μm, although other thicknesses are possible. In FIG. 2D, the first conductive material layer 206 may be patterned to form the bottom electrode 106. The patterning may be performed in any suitable manner. In a non-limiting embodiment, the patterning used to form the bottom electrode 106 may include a lithography and etching process.

Figure 2E:
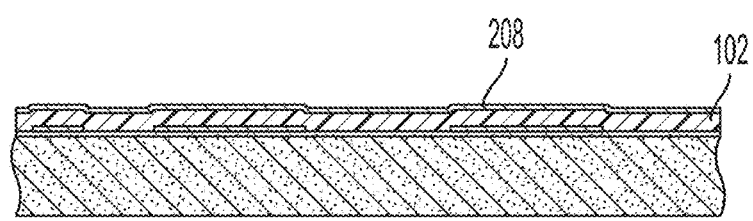

In FIG. 2E, a thin film piezoelectric layer 102 may be deposited on the bottom electrode 106. In a non-limiting embodiment, thin film sputtered AN may be used as the thin film piezoelectric active layer 102. Subsequently, a second conductive material layer 208 may be deposited on the thin film piezoelectric layer 102. According to a non-limiting embodiment, the second conductive material layer 208 may be formed of Molybdenum. However, other suitable conductive materials, including other metals (e.g., Aluminum, Platinum, Titanium-Tungstun (TiW)) may be used. In a non-limiting embodiment, the thin film piezoelectric layer 102 may have a thickness of approximately 2 μm and the second conductive material layer 206 may have a thickness of approximately 0.2 μm.

Figure 2F:
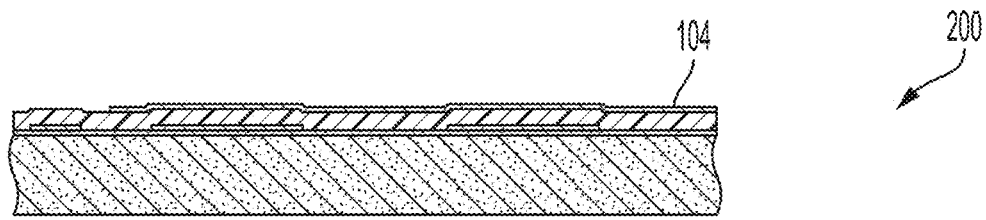

In FIG. 2F, the second conductive material layer 208 may be patterned to form the top electrode 104. The patterning may be performed in any suitable manner. In a non-limiting embodiment, the patterning used to form the top electrode 104 may include a lithography and etching process.

Figure 2G:
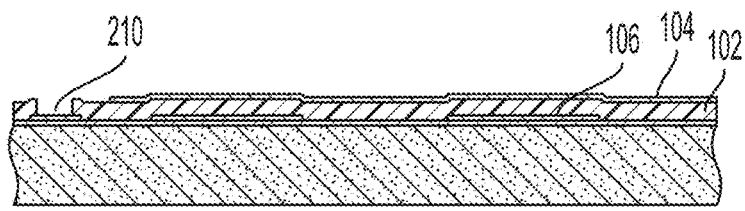

In FIG. 2G, the thin film piezoelectric layer 102 may be etched to form a via 210 to provide a connection to the bottom electrode 106. In this manner, in FIG. 2G, a piezoelectric stack including the thin film piezoelectric active layer 102 and the two electrodes 104, 106 is formed.

Figure 2H:
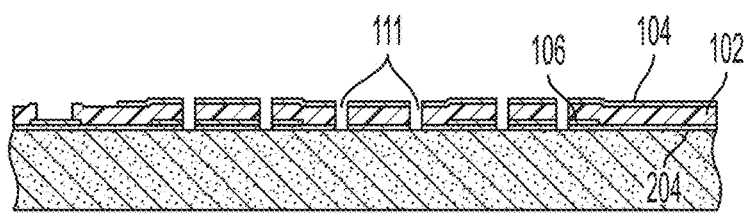

In FIG. 2H, the piezoelectric stack may be patterned to form a plurality of openings 111 to create a mesh structure. In a non-limiting embodiment, the thin film piezoelectric active layer 102, the two electrodes 104, 106, and the thermal oxide layer 204 are patterned to form the openings 111. In some embodiments, the patterning is performed such that edges of the top electrode 104 and the piezoelectric active layer 102 on either side of each opening are aligned in cross-section. The patterning may be performed in any suitable manner. In a non-limiting embodiment, the patterning used to form the openings 111 may include a lithography and etching process. It will be appreciated that the number and diameter of the openings may be selected based on a desired pump volume and droplet size suitable for nebulizers.

Figure 2I:
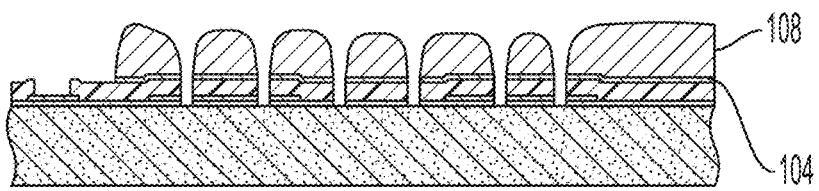

The piezoelectric stack (with the openings 111) may serve as a substrate for electroplating in FIG. 2I. The structure depicted in FIG. 2H may be placed in a electroplating solution and voltage may be applied to the top electrode 104, which results in a metal layer 108 being deposited on the top electrode 104 of the piezoelectric stack. Nickel-Palladium alloys or any other metals (e.g., Chromium, Aluminum) or alloys suitable for nebulizers (e.g., being biocompatible) may be used as the metal layer 108. In some embodiments, the shape of the top electrode 104 and the time period for which the structure is kept in the electroplating solution (i.e., time period for electrodeposition) are controlled or selected to achieve a desired opening diameter in the range of 1-6 µm.

Figure 2J:
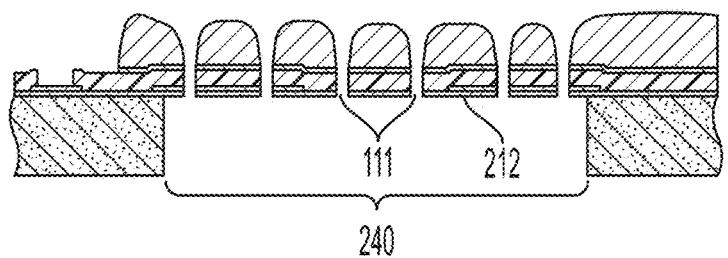

In FIG. 2J, a portion of the substrate 202 may be removed until a bottom surface 212 of the thermal oxide layer 204 and the openings 111 are exposed. Removal of the portion of the substrate may be performed using any suitable technique, for example, chemical-mechanical polishing (CMP) and deep reactive ion etching (DRIE).

In this manner, fabrication process 200 may be used for fabricating the MEMS mesh membrane device 100 with a piezoelectric stack and thick metal layer on the piezoelectric stack.

FIGS. 3A-3J illustrate an alternative fabrication process for fabricating the MEMS mesh-membrane device 100 according to a non-limiting embodiment. The fabrication process 300 (shown in FIGS. 3A-3J) is similar to the fabrication process 200 described above with respect to FIGS. 2A-2J, with the exception of the patterning of the top electrode shown in FIGS. 3H-3I. The fabrication process 300 is briefly described below, but it will be appreciated that the processing steps and materials described above with respect FIGS. 2A-2J apply to FIGS. 3A-3J as well.

Figure 3A:
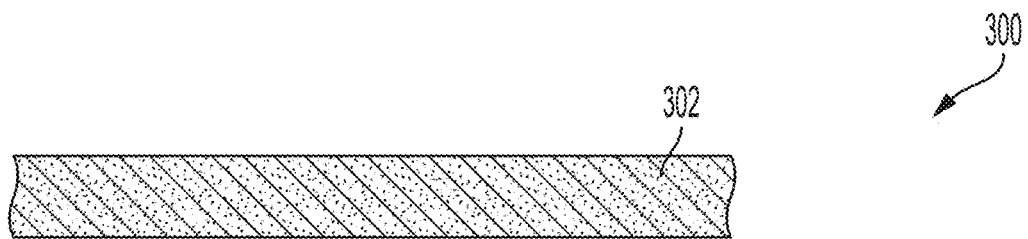
FIGS. 3A-3J illustrate an alternative fabrication process for fabricating the MEMS mesh membrane device of FIG. 1A according to a non-limiting embodiment.
Figure 3B:
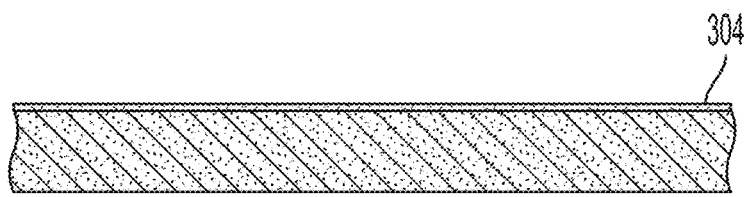
Figure 3C:
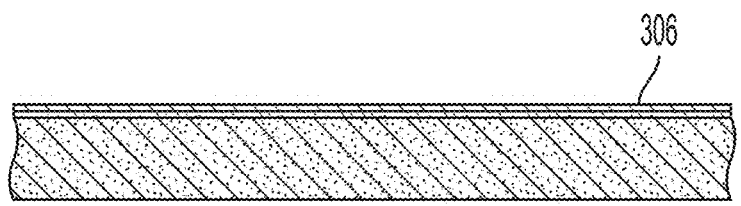
Figure 3D:
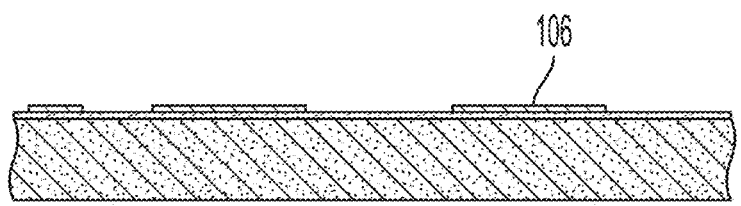
Figure 3E:
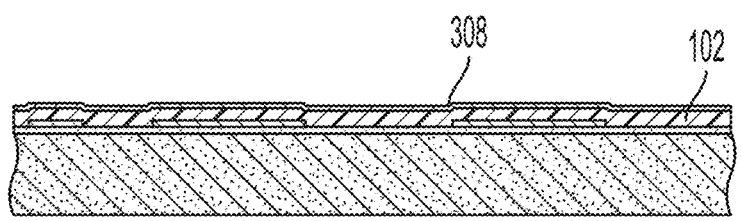
Figure 3F:
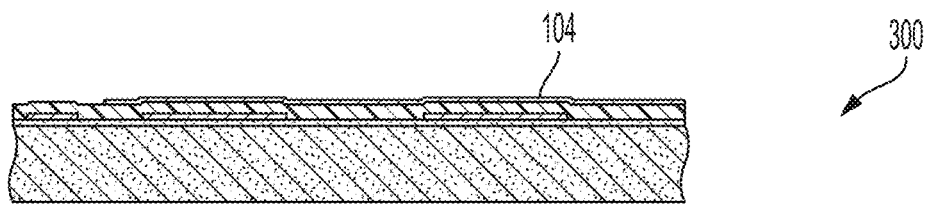
Figure 3G:
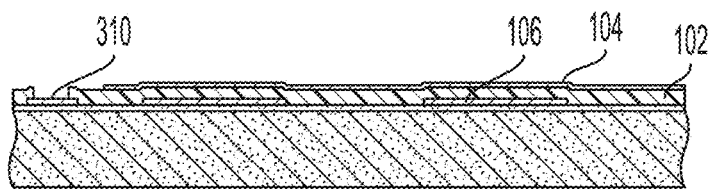

The fabrication process 300 may begin by growing a thermal oxide layer 304 (FIG. 3B) on a substrate 302 shown in FIG. 3A. In FIG. 3C, a first conductive material layer 306 may be deposited on the thermal oxide layer 304. In FIG. 3D, the first conductive material layer 306 may be patterned to form the bottom electrode 106. In FIG. 3E, a thin film piezoelectric layer 102 may be deposited on the bottom electrode 106. Subsequently, a second conductive material layer 308 may be deposited on the thin film piezoelectric layer 102. In FIG. 3F, the second conductive material layer 308 may be patterned to form the top electrode 104. In FIG. 3G, the thin film piezoelectric layer 102 may be etched to form a via 310 to provide a connection to the bottom electrode 106.

Figure 3H:
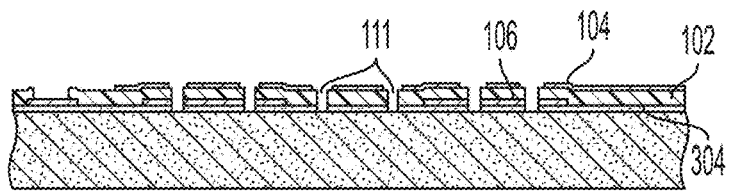
Figure 3I:
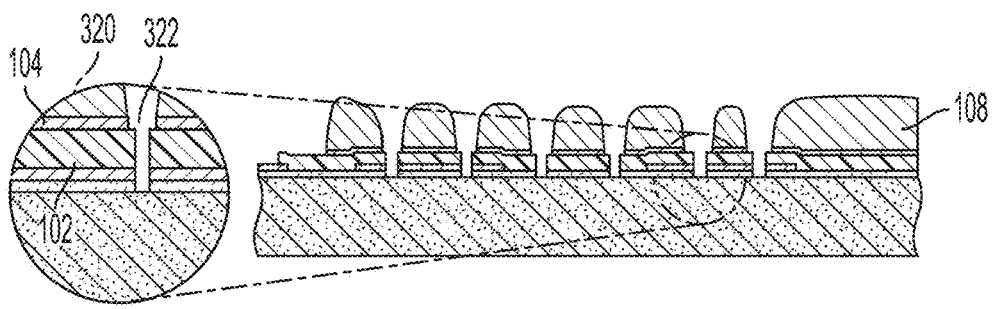

In FIG. 3H, the thin film piezoelectric active layer 102, the two electrodes 104, 106, and the thermal oxide layer 204 are patterned to form a plurality of openings 111, but the patterning is different than that of FIG. 2H. In a non-limiting embodiment, the patterning is performed such that edges of the top electrode 104 and the piezoelectric active layer 102 on either side of each opening are not aligned in cross-section. An exploded view 320 of the edges of the top electrode 104 and the piezoelectric active layer 102 is shown in FIG. 3I. In a non-limiting embodiment, the top electrode 104 may be narrower than the bottom electrode 106 in the in-plane direction. The patterning may be performed in any suitable manner. In a non-limiting embodiment, the patterning used to form the openings 111 may include a lithography and etching process.

The structure depicted in FIG. 3H may be placed in a electroplating solution and voltage may be applied to the top electrode 104, which results in a metal layer 108 being deposited on the top electrode 104 as shown in FIG. 3I. As can be seen in exploded view 320, the metal layer 108 is deposited only on the top electrode 104 and not on an exposed region 322 of the piezoelectric active layer 102. Nickel-Palladium alloys or any other metals (e.g., Chromium, Aluminum) or alloys suitable for nebulizers (e.g., being biocompatible) may be used as the metal layer 108.

Figure 3J:
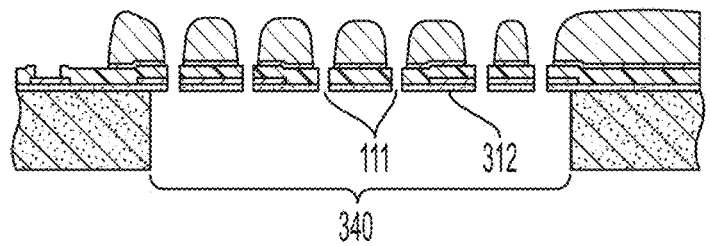

In FIG. 3J, a portion of the substrate may be removed until a bottom surface 312 of the thermal oxide layer 304 and the openings 111 are exposed. In this manner, fabrication process 300 may be alternatively used for fabricating the MEMS mesh membrane device 100 with a piezoelectric stack and thick metal layer on the piezoelectric stack.

It will be appreciated that fabrication process 200 or 300 used for fabricating the MEMS mesh membrane device 100 may beneficially be readily scalable, as opposed to processes requiring assembly of discrete components to make the nebulizer. In addition, the MEMS mesh membrane device 100 may be fabricated using relatively low cost materials, as opposed to devices requiring costly materials such as Palladium.

According to some aspects, as shown in FIG. 2J or FIG. 3J, the electroplated metal layer 108 may have a rounded contour between adjacent openings of the piezoelectric stack in cross-section. Electrodeposition allows for the metal layer 108 to be fabricated with the rounded counter rather than straight edges that are susceptible to cracking. The metal layer 108 with its rounded contour may form a funnel-like shape that can facilitate the flow of the liquid sample through the openings.

In a non-limiting embodiment, the electroplated metal layer 108 may function as a bimorph structure to prompt out-of-plane motion (in the up-down direction) of the piezoelectric active layer 102 and pump the liquid droplets at a desired pump volume. It may not be possible to prompt out-of-plane motion with only the piezoelectric stack, but the presence of the electroplated metal layer 108 prompts required strains upon actuation of the piezoelectric active layer, thereby resulting in out-of-plane motion of the piezoelectric stack. In operation, out-of-plane motion of the piezoelectric stack builds up pressure pushing the sample liquid drug placed in proximity to the metal layer through the openings and ejecting the liquid droplets from the bottom surface of the thermal oxide layer.

Figure 4B:
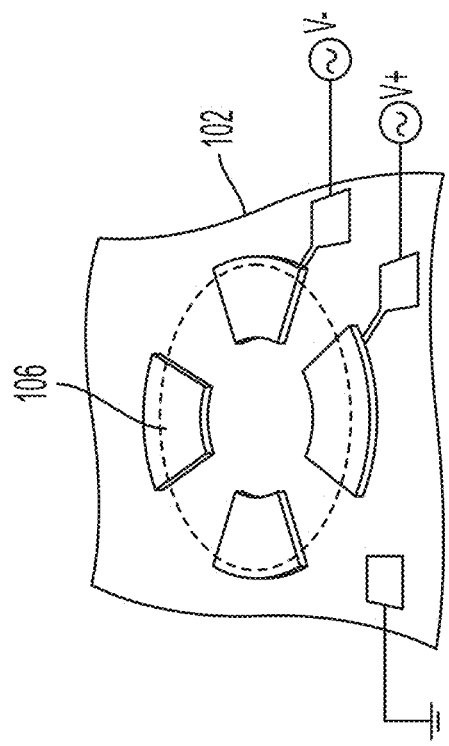
FIGS. 4A-4B illustrate examples of electrode configurations according to a non-limiting embodiment.
Figure 4A:
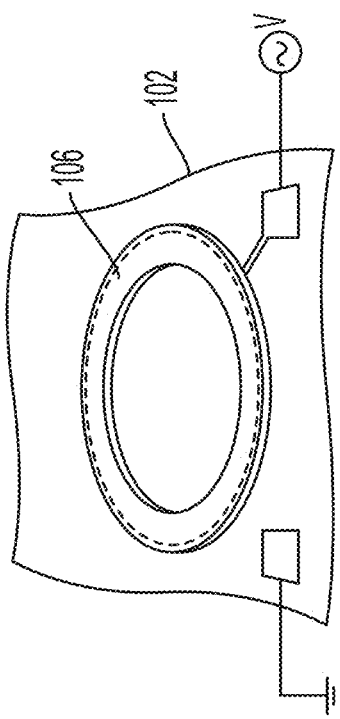

FIGS. 4A-4B illustrate examples of electrode configurations according to non-limiting embodiments. FIGS. 4A and 4B provide examples of placement and configuration of the bottom electrode 106 on the piezoelectric active layer 102. Different configurations of the bottom electrode 106 provide for different vibration patterns of the piezoelectric active layer 102. In some embodiments, the bottom electrode 106 may be patterned in different ways to actuate different modeshapes of the piezoelectric active layer 102. In some embodiments, the dashed line in FIGS. 4A and 4B indicates an opening 240, 340 that is created by removal of the substrate as shown in FIGS. 2J and 3J.

Figure 1B:
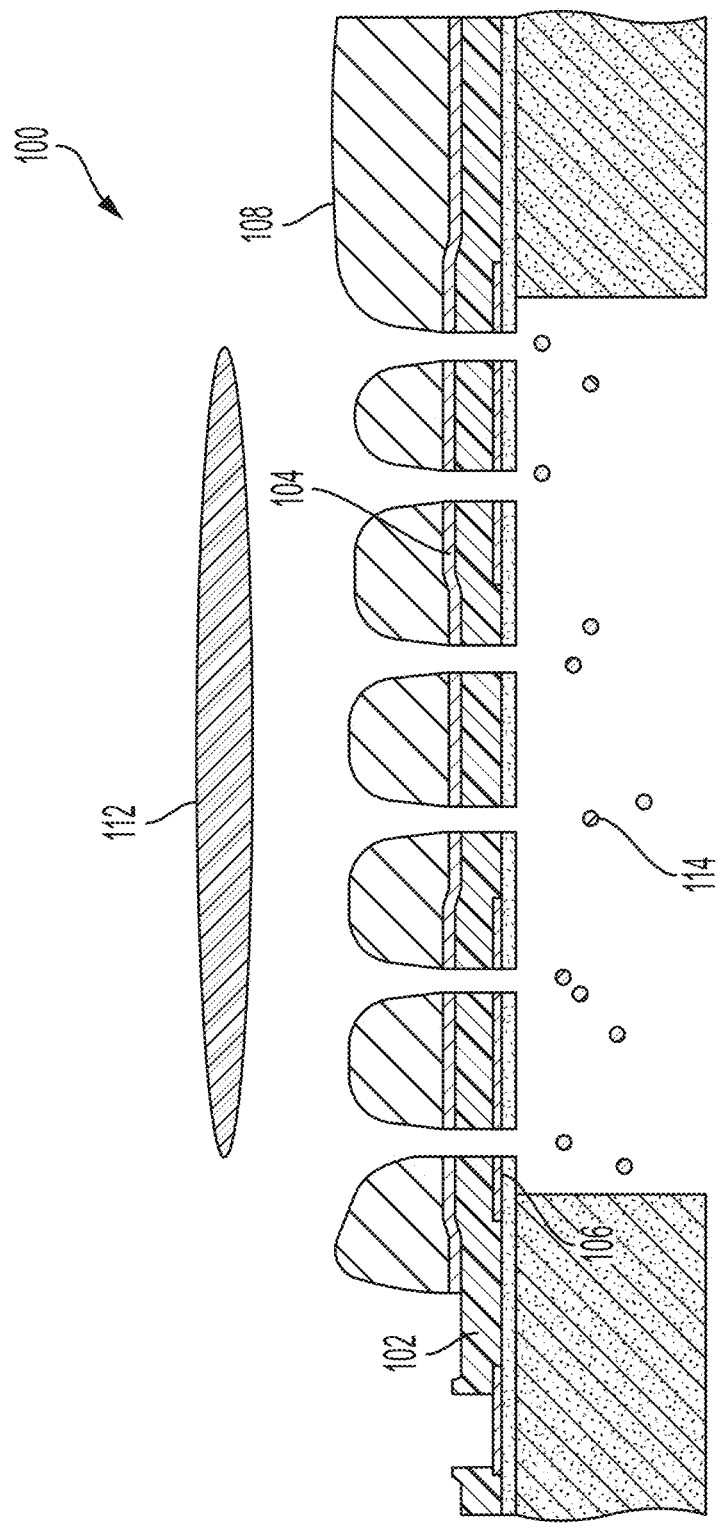
FIG. 1B illustrates the MEMS mesh membrane device of FIG. 1A along with a liquid sample.
Figure 5:
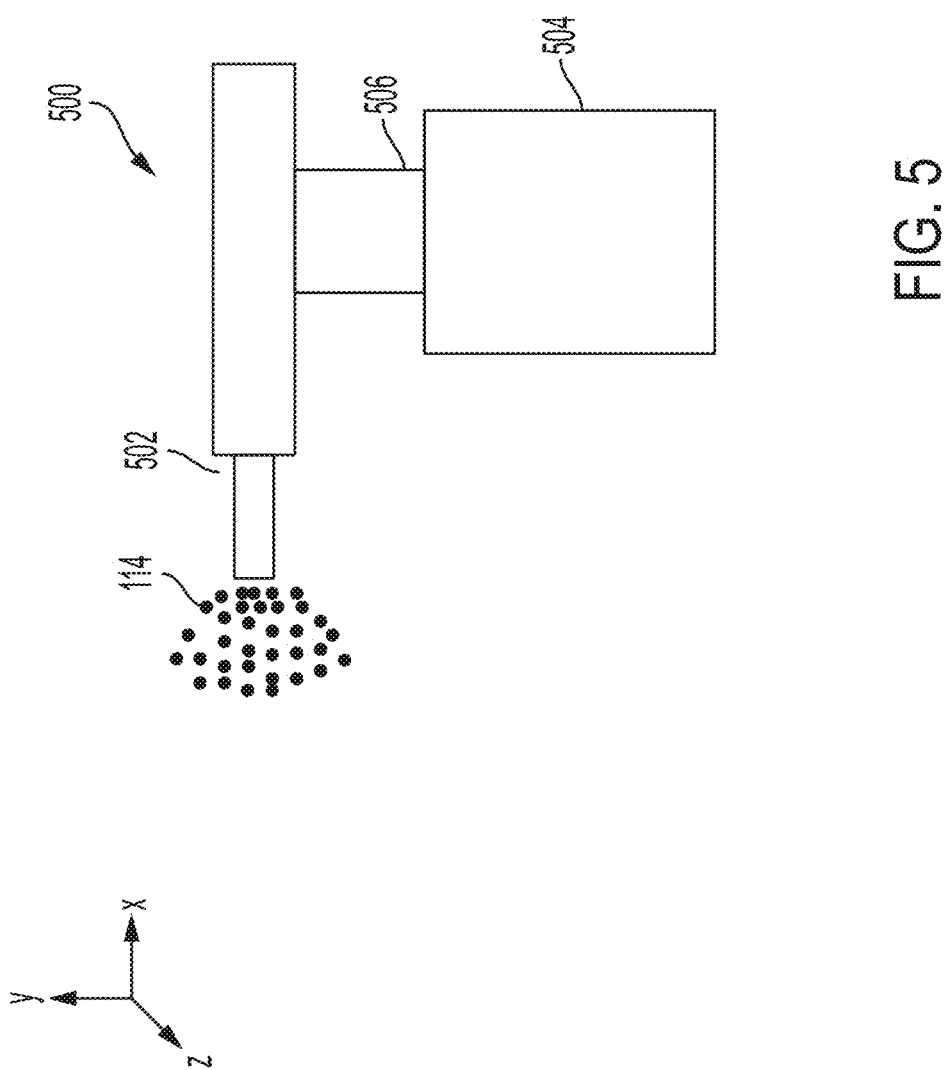
FIG. 5 depicts an example nebulizer that uses the MEMS mesh membrane device of FIG. 1A according to a non-limiting embodiment.

FIG. 5 depicts an example nebulizer 500 that uses the MEMS mesh membrane device of FIG. 1A-FIG. 1B according to a non-limiting embodiment. The nebulizer 500 converts liquid drugs into medical aerosol or droplets that can be inhaled by a user of the nebulizer 500. It will be appreciated that different types of nebulizers having different shapes may use the MEMS mesh membrane device of FIG. 1A-FIG. 1B. For example, FIG. 5 depicts a nebulizer with a mouth piece 502 through which the medical aerosol can be inhaled. However, it will be appreciated that nebulizers with face masks or other devices used for inhalation may be used without departing from the scope of this disclosure.

Nebulizer 500 may include a reservoir 504 for holding a liquid drug. In some embodiments, the MEMS mesh membrane device 100 may be positioned in a variety of locations within the nebulizer 500. In a non-limiting embodiment, the MEMS mesh membrane device 100 may be placed in a region 506 above the reservoir 504. In this embodiment, the MEMS mesh membrane device 100 may be oriented such that the metal layer 108 is facing downwards (e.g., in a −y direction) towards the reservoir 504 and the bottom surface of the thermal oxide layer is facing upwards (e.g., in a y direction) towards the mouth piece 502. In another non-limiting embodiment, the MEMS mesh membrane device 100 may be placed inside or in proximity to the mouth piece 502. In this embodiment, the MEMS mesh membrane device 100 may be oriented such that the bottom surface of the thermal oxide layer faces the mouth piece 502 (e.g., in a −x direction). It will be appreciated that the MEMS mesh membrane device 100 may be placed in different locations and oriented in different ways based on the placement as long as the bottom surface of the thermal oxide layer faces towards the mouth piece 502 for aerosol delivery.

In operation, actuation of the nebulizer by the user causes an electrical signal to be supplied to the top and bottom electrodes 104, 106 of the MEMS mesh membrane device 100, which in turn actuates the piezoelectric active layer 102. Actuation of the piezoelectric active layer 102 results in an out-of-plane motion of the piezoelectric stack. The out-of-plane motion of the piezoelectric stack builds up pressure drawing the liquid drug from the reservoir 504 and pushing the liquid drug through the openings in the form of aerosol droplets towards the mouth piece 502. In a non-limiting embodiment, the openings may each have a diameter in the range of 1-6 µm so as to create aerosol droplets having droplet size 1-6 µm, thereby ensuring efficient and high absorption of the drug into the blood stream.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. A microelectromechanical systems (MEMS) mesh membrane nebulizer, comprising:
   a thin film piezoelectric active layer comprising a plurality of openings;
   first and second electrodes on opposite sides of the thin film piezoelectric active layer; and
   a metal layer on the second electrode having a thickness greater than the second electrode.

2. The MEMS mesh membrane nebulizer of claim 1, wherein the thin film piezoelectric active layer comprises Aluminum Nitride (AlN).

3. The MEMS mesh membrane nebulizer of claim 1, wherein the metal layer has a thickness in a range of 40 µm-100 µm.

4. The MEMS mesh membrane nebulizer of claim 1, wherein at least some of the plurality of openings have a diameter in the range of 1-6 µm.

5. A microelectromechanical systems (MEMS) nebulizer device, comprising:
   a piezoelectric layer comprising a plurality of openings;
   a first electrode on the piezoelectric layer; and
   a metal layer on the first electrode, wherein the metal layer has a thickness in a range of 40 µm-100 µm.

6. A microelectromechanical systems (MEMS) nebulizer device, comprising:
   a piezoelectric layer comprising a plurality of openings;
   a first electrode on the piezoelectric layer; and
   a metal layer on the first electrode, wherein the metal layer has a thickness greater than the first electrode.

7. The MEMS nebulizer device of claim 6, further comprising:
   a second electrode on an opposite side of the piezoelectric layer relative to the first electrode.

8. The MEMS nebulizer device of claim 7, wherein the piezoelectric layer, the first electrode, and the second electrode form a piezoelectric stack, and the plurality of openings are formed in the piezoelectric stack.

9. The MEMS nebulizer device of claim 8, wherein the metal layer is formed on the piezoelectric stack.

10. The MEMS nebulizer device of claim 6, wherein the piezoelectric layer comprises a thin film Aluminum Nitride (AlN) layer.

11. A microelectromechanical systems (MEMS) nebulizer device, comprising:
    a piezoelectric layer comprising a plurality of openings;
    a first electrode on the piezoelectric layer; and
    a metal layer on the first electrode, wherein the metal layer has a thickness greater than a combined thickness of the piezoelectric layer and the first electrode.

12. A microelectromechanical systems (MEMS) nebulizer device, comprising:
    a piezoelectric layer comprising a plurality of openings;
    a first electrode on the piezoelectric layer; and
    a metal layer on the first electrode, wherein the metal layer has a rounded contour.

13. A microelectromechanical systems (MEMS) device, comprising:
    a piezoelectric layer comprising a plurality of openings, wherein at least some of the plurality of openings have a diameter in the range of 1-6 µm;
    a first electrode on the piezoelectric layer; and
    a metal layer on the first electrode.

14. A microelectromechanical systems (MEMS) nebulizer apparatus, comprising:
    a thin film piezoelectric active layer comprising a plurality of openings;
    a first electrode on a first side of the thin film piezoelectric active layer; and a conductive structure on a second side of the thin film piezoelectric active layer opposite the first electrode, the conductive structure comprising a second electrode and a metal layer integrated on the second electrode, such that the second electrode is between the metal layer and the thin film piezoelectric active layer.

15. The MEMS nebulizer apparatus of claim 14, wherein the thin film piezoelectric active layer comprises Aluminum Nitride (AlN).

16. The MEMS nebulizer apparatus of claim 14, wherein the metal layer has a thickness in a range of 40 μm-100 μm.

17. The MEMS nebulizer apparatus of claim 14, wherein at least some of the plurality of openings have a diameter in the range of 1-6 μm.

18. The MEMS nebulizer apparatus of claim 14, wherein the metal layer has a thickness greater than the second electrode.

19. The MEMS nebulizer apparatus of claim 14, wherein the metal layer has a thickness greater than a combined thickness of the thin film piezoelectric active layer and the second electrode.

* * * * *